United States Patent [19]

Bruchmann

[11] Patent Number: 5,329,003
[45] Date of Patent: Jul. 12, 1994

[54] PROCESS FOR THE PREPARATION OF URETDIONE GROUP CONTAINING POLYISOCYANATES

[75] Inventor: Bernd Bruchmann, Ludwigshafen, Fed. Rep. of Germany

[73] Assignee: BASF Aktiengesellschaft, Ludwigshafen, Fed. Rep. of Germany

[21] Appl. No.: 922,296

[22] Filed: Jul. 30, 1992

Related U.S. Application Data

[63] Continuation-in-part of Ser. No. 564,225, Aug. 8, 1990, abandoned.

[51] Int. Cl.$^5$ .......................................... C07D 229/00
[52] U.S. Cl. .................................. 540/202; 548/335.1
[58] Field of Search ........................................ 540/202

[56] References Cited

FOREIGN PATENT DOCUMENTS 0100148 8/1976 Poland .

OTHER PUBLICATIONS

Rechter, Synthesis, p. 463, 1975.
Noack et al., Z. Chem. 26(1) 117, 1986.

*Primary Examiner*—Mukund J. Shah
*Assistant Examiner*—Y. N. Gupta
*Attorney, Agent, or Firm*—Mary E. Golota

[57] ABSTRACT

The invention deals with a process for the preparation of uretdione group containing polyisocyanates comprising reacting monomeric aromatic diisocyanates in the presence of a catalyst whereby imidazoles or benzimidazoles having general structure formulas I or II are used as catalysts

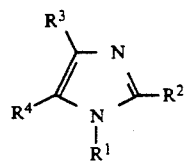

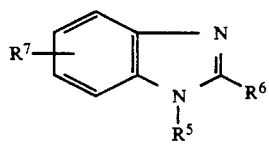

or their mixtures are used whereby $R^1$ through $R^7$ have the meaning cited in claim 1.

12 Claims, No Drawings

PROCESS FOR THE PREPARATION OF URETDIONE GROUP CONTAINING POLYISOCYANATES

This application is a continuation-in-part of and claims priority to copending U.S. application Ser. No. 07/564,225, filed Aug. 8 1990 now abandoned which in turn claims priority to German application 3930669, filed Sep. 14, 1989.

BACKGROUND OF THE INVENTION

1. Field of the Invention

The present invention deals with a process for the preparation of uretdione group containing polyisocyanates comprising reacting monomeric aromatic diisocyanates in the presence of a catalyst.

2. Description of the Related Art

It is basically known to prepare uretdiones by reacting isocyanates in the presence of certain catalysts.

DE-A-3 739 549 discloses a process for the preparation of cycloaliphatic uretdiones in which cycloaliphatic diisocyanates are used as a starting material and pyridine is used as a catalyst.

Richter and Ulrich in *Synthesis,* 1975, pg. 463 describe a process in which benzyl isocyanate is reacted in the presence of 1,2-dimethylimidazole used as a catalyst. However, in this process, a large amount, about 20 percent, of isocyanurate byproducts are obtained. The presence of isocyanurates is undesirable for a number of applications since these are trifunctional and have a tendency to crosslink. Noack and Schwetlick in *Z. Chem.,* 26 (1), pg. 117, 1986 also report this disadvantage of the formation of isocyanurates. When reacting a mixture of 80 weight percent 2,4-toluene diisocyanate and 20 weight percent of 2,6-toluene diisocyanate with 1-methylimidazole, 1,2 -dimethylimidazole or 1-butyl imidazole as catalysts in a mixture of methylethyl ketone and cyclohexane only a maximum of 51% dimer yield is obtained.

Polish patent 100 148 describes reacting aromatic diisocyanates with 1-allyl-2-methylimidazole as a catalyst. However, here the dimer yield is only 50%.

The object of the present invention was to find a process for the preparation of uretdione group containing polyisocyanates which reduces the formation of isocyanurates as far as possible.

The object was met by reacting monomeric aromatic diisocyanates in the presence of a catalyst whereby imidazoles or benzimidazoles having general structural formulas I or II are used as said catalyst:

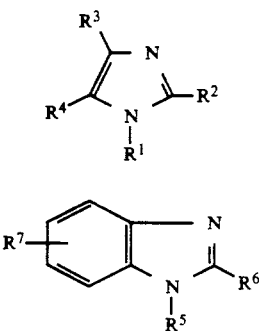

or mixtures thereof are used as said catalysts, whereby $R^1$ and $R^5$ independently are hydrogen atoms; $C_1$- to $C_{16}$- alkyl groups; alkenyl or alkynyl groups having 2 to 16 carbon atoms; aryl groups; alkylaryl or aralkyl groups, whereby the alkyl groups can have from 1 to 10 carbon atoms; amino groups; hydroxy groups or mercapto groups, aminoalkyl groups; alkylamino groups; alkoxy groups; oxyalkyl, alkylthio groups or thioalkyl groups having $C_1$- to $C_{16}$-alkyl groups; or halogen atoms, and $R^2$, $R^3$, $R^4$, $R^6$, $R^7$ have the same meaning as $R^1$ and $R^5$ or are nitro groups; with the proviso that the following compounds are excluded:
1-allyl-2-methylimidazole,
1,2-dimethylimidazole,
1-methylimidazole, and
1-butylimidazole.

The preferred embodiments of the present invention are found in the dependent claims.

It has also been shown that the content of isocyanurates lies below about 2% both when using a water containing solvent as well as an anhydrous solvent.

Typical monomeric aromatic diisocyanates are, for example, 1,5-naphthalene diisocyanate, 4,4'-diphenyl diisocyanate, 1,4-phenylene diisocyanate, as well as more preferably 2,6-toluene diisocyanate, polymethylenepolyphenylenepolyisocyanate, and most preferably 2,4-, and 2,6-toluene diisocyanate and 2,2'- 2,4'- and 4,4'-diphenylmethane diisocyanate.

The reaction can be done neat or in the presence of an inert organic solvent whereby the latter embodiment is preferred. Most preferred is carrying out the reaction in an inert organic solvent with a water content of from 50 to 500 ppm. Toluene, methylethylketone, and n-hexane are examples of suitable solvents. The degree of dryness of the solvent is of great importance. When using commercially available toluene having a water content of about 300 to 500 ppm or commercially available n-hexane having a water content of about 200 to 300 ppm, dimer yields of over 90% are obtained and the product is slightly contaminated by urea. If on the other hand an anhydrous solvent is used having a water content less than 100 ppm the yields of uretdiones are indeed somewhat smaller but the product is almost completely free of ureas. When using both a water-containing as well as anhydrous solvent one obtains a content of isocyanurates less than 2 percent.

The weight ratio of solvent to diisocyanate ranges from 0.1:1 to 10:1. Preferred is using a ratio of from 0.3:1 to 3:1.

The catalyst, likewise in solution, is added to the dissolved diisocyanate at temperatures of from $-10°$ C. to 80° C. more preferably 20° C. to 50° C. while stirring.

Imidazoles I or benzimidazoles II used as catalysts according to the present invention can be used individually or in mixtures. Mixtures of I and II are also possible. Proven most suitable are 1,2,4,5-tetramethylimidazole, 1-(n-butyl)-2,4,5-trimethylimidazole and 1-benzyl-2-methylimidazole. The catalysts are used in quantities of from 0.01 to 50 weight percent, more preferably 0.05 to 1 weight percent based on the diisocyanate. The weight ratio of solvent to imidazole and/or benzimidazole ranges from 1:1 to 100:1, more preferably 10:1 to 60:1.

The resulting reaction product is washed and dried.

The advantages achieved with the instant invention are that the content of undesirable isocyanurate lies below 2 percent and that the purity and yield of the uretdiones can be influenced with the reaction in solution via the degree of dryness of the solvent.

The uretdione group containing polyisocyanates prepared in this fashion can be used to prepare polyurethanes.

EXAMPLES 500 g of monomeric aromatic diisocyanate and 200 g of solvent were treated while stirring with 2.5 g of the corresponding imidazole dissolved in 100 g of solvent at a temperature of 20° C. in the case of toluenediisocyanate(TDI) and at 50° C. in the case of the 4,4'-diphenylmethane diisocyanate(MDI). Stirring continued for 5 hours at this temperature and the resulting suspension was allowed to stand for 16 hours at room temperature. The then solid product was washed twice, each time with 500 g of solvent and dried in a vacuum.

The following table provides information about the imidazoles used as catalysts, the solvents and uretdione yields.

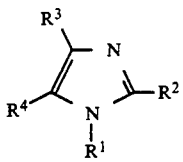

I

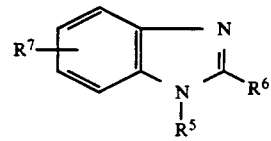

II

TABLE 1

| Example | Diisocyanate | Imidazole | Solvent | Yield of Uretdione [%] |
|---|---|---|---|---|
| 1 | 2,4-TDI | 1,2,4,5-tetra-methylimidazole | toluene | 96 |
| 2 | 2,4-TDI | 1,2,4,5-tetra-methylimidazole | toluene, dried | 81 |
| 3 | 2,4-TDI | 1,2,4,5-tetra methylimidazole | n-hexane | 95 |
| 4C[1] | 2,4-TDI | 1-allyl-2-methyl-imidazole | toluene | 50 |
| 5 | 2,4-TDI | 1-n-butyl-2,4,5-trimethylimidazole | toluene | 95 |
| 6 | 2,4-TDI | 1-n-butyl-2,4,5-trimethylimidazole | toluene, dried | 60 |
| 7 | 2,4-TDI | 1-benzyl-2-methylimidazole | toluene | 93 |
| 8 | 2,4-TDI | 1-benzyl-2-methylimidazole | toluene, dried | 44 |
| 9 | TDI[2] | 1,2,4,5-tetra-methylimidazole | toluene | 60 |
| 10C[3] | TDI[2] | 1-methylimidazole | methylethyl-ketone/cyclohexane | 46 |
| 11 | MDI | 1,2,4,5-tetra methylimidazole | toluene | 83 |
| 12 | MDI | 1-aminopropyl-2-methylimidazole | methylethyl-ketone | 92 |
| 13 | MDI | 1-aminopropyl-2-methylimidazole | methylethyl-ketone, anhydrous | 65 |
| 14 | MDI | 1-hydroxymethyl-2, 4-dimethyl imidazole | methylethyl-ketone | 89 |
| 15 | MDI | 1-hydroxymethyl-2, 4-dimethyl | methylethyl-ketone, anhydrous | 63 |

[1]Comparison example in accordance with Polish patent 100 148 using pure 2,4-TDI.
[2] 80:20 mixture of 2,4- and 2,6-TDI.
[3]Comparison example according to Novak and Schwetlick, Z. Chen p. 117 (1986).

or mixtures thereof are used as said catalysts, whereby $R^1$ and $R^5$ independently are $C_1$- to $C_{16}$- alkyl groups; alkenyl or alkynyl groups having 2 to 16 carbon atoms; aryl groups; alkylaryl or aralkyl groups, whereby the alkyl groups can have from 1 to 10 carbon atoms, amino groups; hydroxyl groups or mercapto groups; aminoalkyl groups; alkylamino groups; alkoxy groups; oxyalkyl, alkylthio groups or thioalkyl groups having $C_1$- to $C_{16}$-alkyl groups or halogen atoms, $R^2$, $R^3$, $R^4$, $R^6$, or $R^7$ have the same meaning as $R^1$ and $R^5$ or are nitro groups and $R^3$, $R^4$ can be hydrogen provided that $R^1$ is not alkyl, alkenyl or alkynyl;

with the proviso that the following compounds are excluded:
1-allyl-2-methylimidazole,
1,2-dimethylimidazole;
1-methylimidazole and
1-butylimidazole,

We claim:
1. A process for the preparation of uretdione group containing polyisocyanates, comprising reacting monomeric aromatic diisocyanates selected from the group consisting of 1,5-naphthalenediisocyanate, 1,4-phenylenediisocyanate, 4,4'-diphenyldiisocyanate, polymethylenepolyphenylenepolyisocyanate, 2,4- and 2,6-toluenediisocyanate, 2,2'-, 2,4'-, and 4,4'-diphenylmethane diisocyanate, and mixtures thereof in the presence of a catalyst wherein imidazoles or benzimidazoles having general structural formulas I or II are used as said catalysts;

wherein the reaction product contains less than about 2 weight percent isocyanurates.

2. The process of claim 1 wherein 1,2,4,5-tetramethylimidazole 1-(n-butyl)-2,3-5-trimethylimidazole, or 1-benzyl-2-methylimidazole are used as said imidazole I.

3. The process of claims 1 or 2 wherein the reaction is carried out in an inert organic solvent having a water content of from 50 to 500 ppm.

4. The process of claim 1 wherein said catalyst is selected from the group consisting of 1-aminopropyl-2-methylimidazole and 1-hydroxymethyl-2,4-dimethylimidazole.

5. The process of claim 1 wherein said monomeric aromatic diisocyanate is selected from the group consisting of 2,4- and 2,6-toluenediisocyanate and mixtures thereof.

6. The process of claim 2 wherein said monomeric aromatic diisocyanate is selected from the group consisting of 2,4- and 2,6-toluenediisocyanate and mixtures thereof.

7. The process of claim 3 wherein said monomeric aromatic diisocyanate is selected from the group consisting of 2,4- and 2,6-toluenediisocyanate and mixtures thereof.

8. The process of claim 4 wherein said monomeric aromatic diisocyanate is selected from the group consisting of 2,4- and 2,6-toluenediisocyanate and mixtures thereof.

9. The process of claim 1 wherein said monomeric aromatic diisocyanate is selected from the group consisting of 2,2'-, 2,4'-, and 4,4'-methylenediphenylenediisocyanate and mixtures thereof.

10. The process of claim 2 wherein said monomeric aromatic diisocyanate is selected from the group consisting of 2,2'-, 2,4'-, and 4,4'-methylenediphenylenediisocyanate and mixtures thereof.

11. The process of claim 3 wherein said monomeric aromatic diisocyanate is selected from the group consisting of 2,2'-, 2,4'-, and 4,4'-methylenediphenylenediisocyanate and mixtures thereof.

12. The process of claim 4 wherein said monomeric aromatic diisocyanate is selected from the group consisting of 2,2'-, 2,4'-, and 4,4'-methylenediphenylenediisocyanate and mixtures thereof.

* * * * *